(12) United States Patent
Kroll et al.

(10) Patent No.: US 7,231,255 B1
(45) Date of Patent: *Jun. 12, 2007

(54) SYSTEM AND METHOD FOR REDUCING PAIN ASSOCIATED WITH CARDIOVERSION SHOCKS GENERATED BY IMPLANTABLE CARDIAC STIMULATION DEVICES

(75) Inventors: Mark W. Kroll, Simi Valley, CA (US); Gabriel A. Mouchawar, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 427 days.

This patent is subject to a terminal disclaimer.

(21) Appl. No.: 10/855,840

(22) Filed: May 26, 2004

(51) Int. Cl.
*A61N 1/34* (2006.01)
*A61N 1/38* (2006.01)
*A61N 1/39* (2006.01)

(52) U.S. Cl. .................. 607/46; 607/5; 607/7
(58) Field of Classification Search .............. 607/5, 607/7, 46
See application file for complete search history.

(56) References Cited

U.S. PATENT DOCUMENTS

| | | | |
|---|---|---|---|
| 5,782,882 A * | 7/1998 | Lerman et al. .............. | 607/10 |
| 5,830,236 A | 11/1998 | Mouchawar et al. .......... | 607/5 |
| 5,906,633 A | 5/1999 | Mouchawar et al. .......... | 607/5 |
| 5,987,354 A | 11/1999 | Cooper et al. ................ | 607/5 |
| 6,091,989 A | 7/2000 | Swerdlow et al. ............ | 607/5 |
| 6,327,500 B1 | 12/2001 | Cooper et al. ................ | 607/5 |
| 6,438,418 B1 | 8/2002 | Swerdlow et al. ............ | 607/5 |
| 6,519,493 B1 | 2/2003 | Florio et al. .................. | 607/9 |

FOREIGN PATENT DOCUMENTS

| | | |
|---|---|---|
| WO | WO 99/19021 | 4/1999 |
| WO | WO 99/51300 | 10/1999 |
| WO | WO 01/21255 | 3/2001 |

* cited by examiner

*Primary Examiner*—Carl Layno
*Assistant Examiner*—Tammie K. Heller

(57) ABSTRACT

Techniques are provided for generating pre-pulse pain inhibition (PPI) pulses and subsequent main cardioversion shocks. The PPI pulses are relatively low-voltage pulses each having a chevron-shaped waveform. The main shocks are relatively high-voltage shocks each having a plateau-shaped waveform. By employing plateau-shaped waveforms for the main shocks, a greater cardiac membrane response can be achieved at an equivalent peak voltage as compared to conventional shock waveforms. Peak voltage is a significant contributor to pain caused by cardioversion shocks. Hence, by using the plateau-shaped waveform, pain reduction can be achieved without loss of shock effectiveness. Moreover, by employing chevron-shaped PPI pulses in combination with plateau-shaped main shocks, a relatively simple shocking circuit having a single high-voltage shocking capacitor may be used, thus eliminating the need for both low-voltage PPI capacitors and higher voltage main shock capacitors. The shocking circuit includes a low-pass resistive-capacitive filter.

14 Claims, 8 Drawing Sheets

SYSTEM AND METHOD FOR REDUCING PAIN ASSOCIATED WITH CARDIOVERSION SHOCKS GENERATED BY IMPLANTABLE CARDIAC STIMULATION DEVICES

CROSS-REFERENCE TO RELATED APPLICATIONS

This application is related to copending U.S. patent application Ser. No. 10/855,654, filed May 26, 2004, titled "System and Method for Reducing Pain Associated with Cardioversion Shocks Generated by Implantable Cardiac Stimulation Devices".

FIELD OF THE INVENTION

The invention generally relates to implantable cardiac stimulation devices such implantable cardioverter/defibrillators (ICDs) and, in particular, to techniques for generating smoothed cardioversion shocks to reduce pain associated with the shock and also to techniques for generating pain inhibition pulses prior to the shock.

BACKGROUND OF THE INVENTION

Atrial fibrillation ("AF") is a cardiac arrhythmia wherein the atria beat chaotically, thereby providing generally poor conduction of blood into the ventricles of the heart and hence reducing the flow of blood throughout the body. AF has been shown to lead to long-term health problems such as increased risk of thrombolytic stroke. AF can also cause reduced cardiac efficiency, irregular ventricular rhythm and unpleasant symptoms such as palpitations and shortness of breath. In some cases, AF can trigger ventricular fibrillation (VF) wherein the ventricles of the heart beat chaotically thereby providing little or no blood flow to the brain and other organs. VF, if not terminated, is usually fatal.

Hence, it is highly desirable to terminate AF should it arise and revert the atria to a normal rhythm. The current, most common therapy for atrial fibrillation is the administration of anti-arrhythmic drugs that control atrial and ventricular rates during AF. However, these drugs can actually be proarrhythmic, causing the arrhythmia to worsen. At best, anti-arrhythmic drugs appear to provide short-term therapy. Another technique for terminating AF is to administer an electrical cardioversion shock to the atria of the heart. The cardioversion shock, if successful, terminates the chaotic pulsing of the atria and causes the atria to resume a normal beating pattern. Patients prone to AF may have an ICD implanted therein capable of detecting AF and automatically administering one or more cardioversion shocks to terminate AF. Typically, about two joules of energy is administered within each cardioversion shock at an initial voltage of between 100 to 500 volts (V). The duration of the pulse is usually between 5–15 milliseconds (ms) and is a descending voltage capacitive discharge waveform. State of the art ICDs are also capable of detecting a wide variety of other heart arrhythmias, such as VF, and for administering appropriate therapy as well. For VF, the ICD administers a much stronger cardioversion shock (referred to as a defibrillation shock) directly to the ventricles of the heart. The defibrillation shock typically has at least ten to twelve joules of electrical energy. Note that, herein, "cardioversion" generally refers to the delivery of any electrical shock intended to synchronize action potentials of myocardial cells within the heart to terminate arrhythmias. Defibrillation, herein, refers to a type of cardioversion specifically intended to terminate fibrillation.

Although atrial cardioversion shocks have been found to be effective for terminating AF within many patients, the shocks can be quite painful. One reason is that the patient is typically conscious and alert at the time the shock is administered. In contrast, the much stronger ventricular defibrillation shocks for terminating VF are typically not administered until the patient has lost consciousness and hence the patient may feel only residual chest pain upon being revived. Because AF is not usually immediately life-threatening, painful cardioversion shocks for its treatment are often perceived by patients as being worse than the condition itself and therefore not tolerated. Indeed, anxiety arising from the fear of receiving a painful cardioversion shock may be sufficient to raise the heart rate sufficiently to trigger the shock. As some patients have hundreds of AF episodes per year, techniques for reducing the pain associated with cardioversion shocks are highly desirable. It is also desirable to reduce pain associated with ventricular defibrillation shocks. Although patients receiving ventricular defibrillation shocks are usually unconscious when the shock is delivered, in some cases, such shocks are erroneously delivered while the patient is conscious due to false-positive VF detection, resulting in considerable patient pain.

One method for reducing pain arising from cardioversion shocks involves altering the stimulation waveform of the shock to, for example, reduce or smooth initial voltage peaks. See, for example, U.S. Pat. No. 5,830,236, to Mouchawar et al., entitled "System for Delivering Low Pain Therapeutic Electrical Waveforms to the Heart" and U.S. Pat. No. 5,906,633, also to Mouchawar et al., entitled "System for Delivering Rounded Low Pain Therapeutic Electrical Waveforms to the Heart." Shock smoothing is illustrated by way of FIGS. 1 and 2. FIG. 1 illustrates a conventional cardioversion shock waveform 1 (shown in V) along with a resulting cardiac membrane response 2. Herein, the cardiac membrane response is shown in arbitrary response units for the purposes of comparison. The shock waveform is biphasic, with an initial peak voltage of 100 V. The peak of the resulting cardiac membrane response is at about 50 response units. Peak voltage is typically regarded as the primary determinant of shock pain; whereas the peak cardiac membrane response is typically regarded as the primary indicator of shock effectiveness. Hence, with the conventional shock waveform of FIG. 1, the effectiveness of the shock is only about 50 cardiac response units; the resulting pain is associated with 100 V. FIG. 2, in contrast, illustrates a smoothed cardioversion waveform 3 along with a resulting cardiac membrane response 4, shown in the same arbitrary response units of FIG. 1 for comparison purposes. The shock waveform of FIG. 2 is smoothed so as to reduce peak voltage to about 70 V. The peak of the resulting cardiac membrane response is still about 45 response units. Hence, with the smoothed shock waveform of FIG. 2, the cardioversion shock is almost as effective as with the non-smoothed waveform of FIG. 1; whereas the resulting pain is significantly lower, i.e. the resulting pain is associated with a peak voltage of only about 70 V rather than with a peak voltage of 100 V. One way to generate the smoothed waveform of FIG. 2 is to start with a higher initial capacitor voltage (about 160 V) than the non-smoothed waveform of FIG. 1 and then use resistive loss to lower the voltage as needed. The capacitor voltage is shown by way of phantom line 5, which decreases exponentially. The capacitor voltage at each point in time must be at least as great as the output pulse being generated at that same point in time. During times when the capacitor voltage is greater than the corresponding output shock voltage, the additional energy is dissipated as heat. Thus, pain reduction is achieved at the expense of consuming somewhat greater energy per shock. Note also that the graphs of FIGS. 1 and 2, and all other graphs provided herein, include stylized representations of the parameters being illustrated. This is done so as to more clearly illustrate pertinent features of those parameters. The graphs should not be construed as illustrating actual clinically-detected parameters.

Thus, smoothed waveforms of the type shown in FIG. 2 can be effective in reducing the resulting pain. It would be desirable, however, to achieve an even greater amount of pain reduction without reducing shock effectiveness. It is to that end that certain aspects of the invention are directed. Moreover, it would also be desirable to provide a relatively simple circuit capable of generating improved shock waveforms and other aspects of the invention are directed to that end.

Another method for reducing pain arising from cardioversion shocks is to deliver a pre-pulse pain inhibition (PPI) pulse prior to the main shock. See, for example, U.S. Pat. No. 6,091,989 to Swerdlow et al., entitled "Method and Apparatus for Reduction of Pain from Electric Shock Therapies." With PPI techniques, a relatively weak stimulus (the PPI pulse) is applied to the patient shortly before a main cardioversion shock. The human pain perception system responds to the weak stimulus in such manner that the pain associated with the subsequent main cardioversion shock is reduced or otherwise inhibited. PPI techniques typically employ either a single relatively long, low-voltage PPI pulse or a single relatively short, high-voltage PPI pulse. The long, low-voltage PPI pulse is usually delivered at about 12–20 V. The shorter, high-voltage PPI pulse is usually delivered at the voltage of the subsequent main cardioversion shock. Each has its respective advantages and disadvantages.

Conventional low-voltage and high-voltage PPI pulses are illustrated by way of the timing diagrams of FIG. 3, which show a low-voltage PPI pulse 6 followed by a high-voltage main cardioversion shock 7 and which also show a much shorter high-voltage PPI pulse 8 followed also by a main shock 9. All waveforms of FIG. 3 are monophasic, though biphasic waveforms may instead be employed. None of the waveforms has been smoothed. The exemplary low-voltage PPI pulse and its subsequent main shock are of substantially equal duration (typically about 1–10 ms) but the PPI pulse has an initial peak voltage of only about 20 V whereas the main shock has an initial peak voltage of about 100 V. The exemplary high-voltage PPI pulse is much shorter than its subsequent main shock (e.g., as short as 0.1 ms as opposed to 1–10 ms) but is of equal voltage (again about 100 V). In each case, the PPI pulse is provided to reduce the pain perceived by the patient during the subsequent main cardioversion shock. The time scale of FIG. 3 is arbitrary but, typically, PPI pulses are delivered 30–500 ms prior to the main cardioversion shock.

A significant advantage of generating a short, high-voltage PPI pulse at the same voltage as the main shock is that only a single shocking capacitor is required, precharged to the main shock voltage. To instead deliver a PPI pulse at a low-voltage followed by a main shock at a much higher voltage, two shocking capacitors are usually required—one precharged to the low-voltage and the other precharged to the high-voltage. However, high-voltage PPI pulses can be painful in and of themselves thus reducing their effectiveness in overall pain reduction. Hence, low-voltage PPI pulses are typically preferred despite the need for an extra shocking capacitor. In this regard, note that capacitors used for generating conventional pacing pulses ordinarily cannot be employed to also generate low-voltage PPI pulses, which typically require a somewhat higher voltage than the pacing pulses.

One technique for delivering high-voltage PPI pulses that are not painful in and of themselves is to utilize extremely short duration "sliver" pulses, which are typically only about 25–50 microseconds (µs) in duration. The sliver pulses are nevertheless sufficient to provide pain inhibition. Preferably, the high-voltage PPI sliver pulses are delivered between electrodes implanted within the heart, such as between a right ventricular (RV) coil and a superior vena cava (SVC) coil, so that high-voltage can be used without risk of significant pain arising from the PPI pulse itself. In particular, pain is reduced by generating the PPI pulse away from the device can or housing. Pulses instead generated using the device can as a return electrode may stimulate sensitive skin nerves and sensitive alpha motor neurons in the pectorals. The subsequent main cardioversion shock is preferably delivered using widely spaced electrodes, such as between the SVC coil and the housing of the implanted device, to ensure maximum likelihood of success. Sliver pulses are discussed in U.S. patent application Ser. No. 10/428,222 of Kroll et al., entitled "System and Method for Generating Pain Inhibition Pulses Using an Implantable Cardiac Stimulation Device," filed Apr. 30, 2003, which is incorporated by reference herein.

Although the techniques of Kroll et al. are very effective, there is room for still further improvement. In particular, it would be desirable to provide an improved PPI sliver pulse waveform that can be safely delivered using the device can as a return electrode without risk of adversely stimulating sensitive skin nerves and sensitive alpha motor neurons in the pectorals. To this end, it would be desirable to provide a low-voltage PPI sliver pulse that can be generated without requiring an extra shocking capacitor and other aspects of the invention are directed to that end. Moreover, it would be especially desirable to provide a single, relatively simple circuit using a single shocking capacitor that is capable of generating both an improved low-voltage PPI pulse and an improved high-voltage smoothed shock and still other aspects of the invention are directed to that end.

SUMMARY

Various systems and methods are provided for reducing pain associated with cardioversion shocks delivered by implantable cardiac stimulation devices.

In accordance with a first embodiment, a cardioversion technique is provided wherein a cardioversion shock having a plateau-shaped waveform is generated using a shocking circuit having a low-pass resistive-capacitive (RC) filter and then the plateau-shaped shock is applied to cardiac tissue of the patient. By employing a plateau-shaped waveform, pain reduction can be achieved as compared to non-smoothed shocks or shocks smoothed in accordance with conventional techniques, at least for equivalent peak voltages. In particular, a greater cardiac membrane response is achieved at an equivalent peak voltage using the plateau-shaped waveform. Accordingly, for a given peak voltage, a more effective shock is delivered. Alternatively, for a given level of shock effectiveness, a lower peak voltage may be employed, thus reducing pain. In one specific example, a first phase of a biphasic plateau-shaped shock has an initial short rise time of about 0.5 ms, followed by a plateau time of about 9 ms wherein the voltage remains constant, and then a short drop of about 0.5 ms back to a baseline voltage. Using the exemplary plateau-shaped waveform with a peak voltage set to 100 V, the level of cardiac membrane response is typically at least twice that achieved by a conventional biphasic shock also having a peak voltage of 100 V.

In accordance with a second embodiment, a pain inhibition technique is provided wherein a PPI pulse having a chevron-shaped waveform is generated and then applied to heart tissue of the patient. Preferably, a plateau-shaped main shock having a much higher peak voltage is then generated and also applied to the heart tissue. The lower voltage PPI pulse serves to reduce the amount of pain perceived by the patient in response to the main shock. The lower voltage PPI pulse may be an extremely short "sliver" pulse on the order of only 40 µs in duration. By employing a low-voltage PPI pulse, the pulse may be advantageously delivered between an electrode implanted within the heart and the device housing, without any significant risk that the PPI pulse itself while cause patient pain as with high-voltage PPI pulses. Moreover, by employing a chevron-shaped PPI pulse in combination with a plateau-shaped main shock, a relatively simple shocking circuit with a single high-voltage shocking capacitor may be used, thus eliminating the need for both low-voltage PPI capacitors and much higher voltage main shock capacitors.

In accordance with a third embodiment, a shocking circuit is provided for use in an implantable cardiac stimulation device for selectively generating either a plateau-shaped output waveform or a chevron-shaped output waveform. The shocking circuit comprises a main storage capacitor operative to hold a shock delivery charge, a low-pass resistive-capacitive (RC) filter, and switching circuitry operative to selectively discharge the main storage capacitor through the low-pass RC filter and into heart tissue. By incorporating a low-pass RC filter into the shocking circuit, both a low-voltage chevron-shaped PPI pulse and a high-voltage plateau-shaped main shock can be generated using charge delivered by a single high-voltage main storage capacitor. In one example, the switching circuit includes an H-bridge circuit and a chopping switch, and the low-pass RC filter has a time constant in the range of 80 µs–120 µs. Control circuitry is provided to control the switching circuit to initially discharge a first portion of charge stored in the main storage capacitor through the low-pass RC filter to generate the chevron-shaped PPI pulse and then to discharge a second portion of charge from the main storage capacitor also through the low-pass RC filter to generate the plateau-shaped main shock. In one specific example, the chevron-shaped PPI pulse has a peak voltage of about 25 V and an overall duration of about 40 µs; whereas the plateau-shaped main shock has a peak voltage of about 250 V and an overall duration of about 15 ms.

The techniques and circuits of the invention are advantageously employed to generate cardioversion shocks for delivering in response to AF but may also be used to deliver other types of cardioversion shocks, such as defibrillation shocks.

BRIEF DESCRIPTION OF THE DRAWINGS

Further features and advantages of the invention may be more readily understood by reference to the following description taken in conjunction with the accompanying drawings, in which.

DESCRIPTION OF THE PREFERRED EMBODIMENTS

The following description includes the best mode presently contemplated for practicing the invention. The description is not to be taken in a limiting sense but is made merely for the purpose of describing the general principles of the disclosed embodiments. The scope of the invention should be ascertained with reference to the issued claims. In the description that follows, like numerals or reference designators will be used to refer to like parts or elements throughout.

An overview of an implantable device configured to implement the invention is first provided with reference to FIGS. 4–5, then the techniques and circuits of the invention are described in greater detail with reference to FIGS. 6–10.

Overview of Implantable Device

Figure 4:
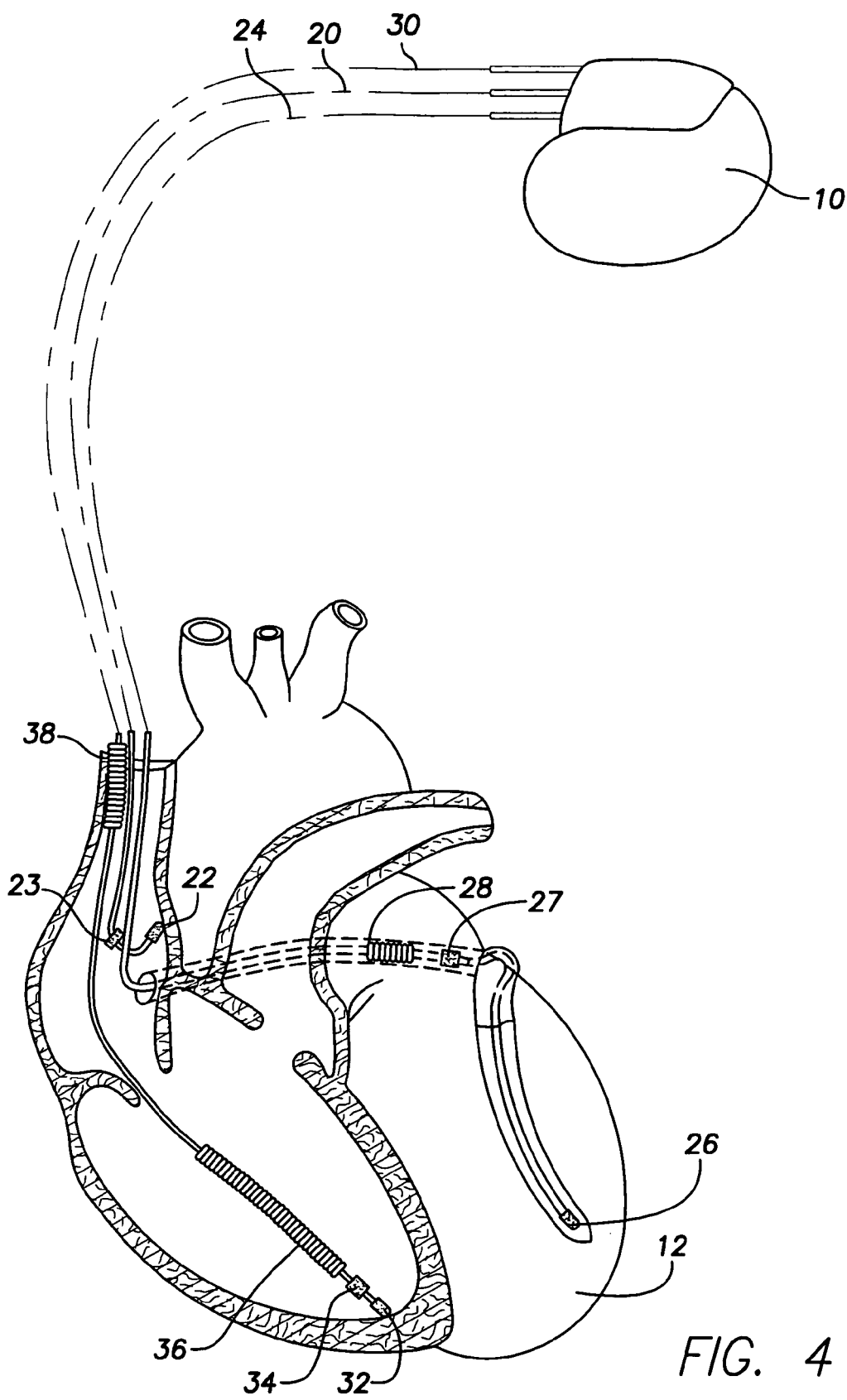
FIG. 4 is a simplified diagram illustrating an implantable stimulation device in electrical communication with at least three leads implanted into the heart of a patient for delivering multi-chamber stimulation and cardioversion therapy.

FIG. 4 illustrates a stimulation device 10 in electrical communication with the heart 12 of a patient by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the right atrial appendage and an atrial ring electrode 23. To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the heart by way of an implantable right ventricular lead 30 having, in this embodiment, a right ventricular tip electrode 32, a right ventricular ring electrode 34, a right ventricular RV coil electrode 36, and an SVC coil electrode 38. Typically, the right ventricular lead 30 is transvenously inserted into the heart so as to place the right ventricular tip electrode 32 in the right ventricular apex so that the RV coil electrode is positioned in the right ventricle and the SVC coil electrode 38 is positioned in the superior vena cava. Accordingly, the right ventricular lead 30 is capable of receiving cardiac signals, and delivering stimulation in the form of pacing and shock therapy to the right ventricle.

Figure 5:
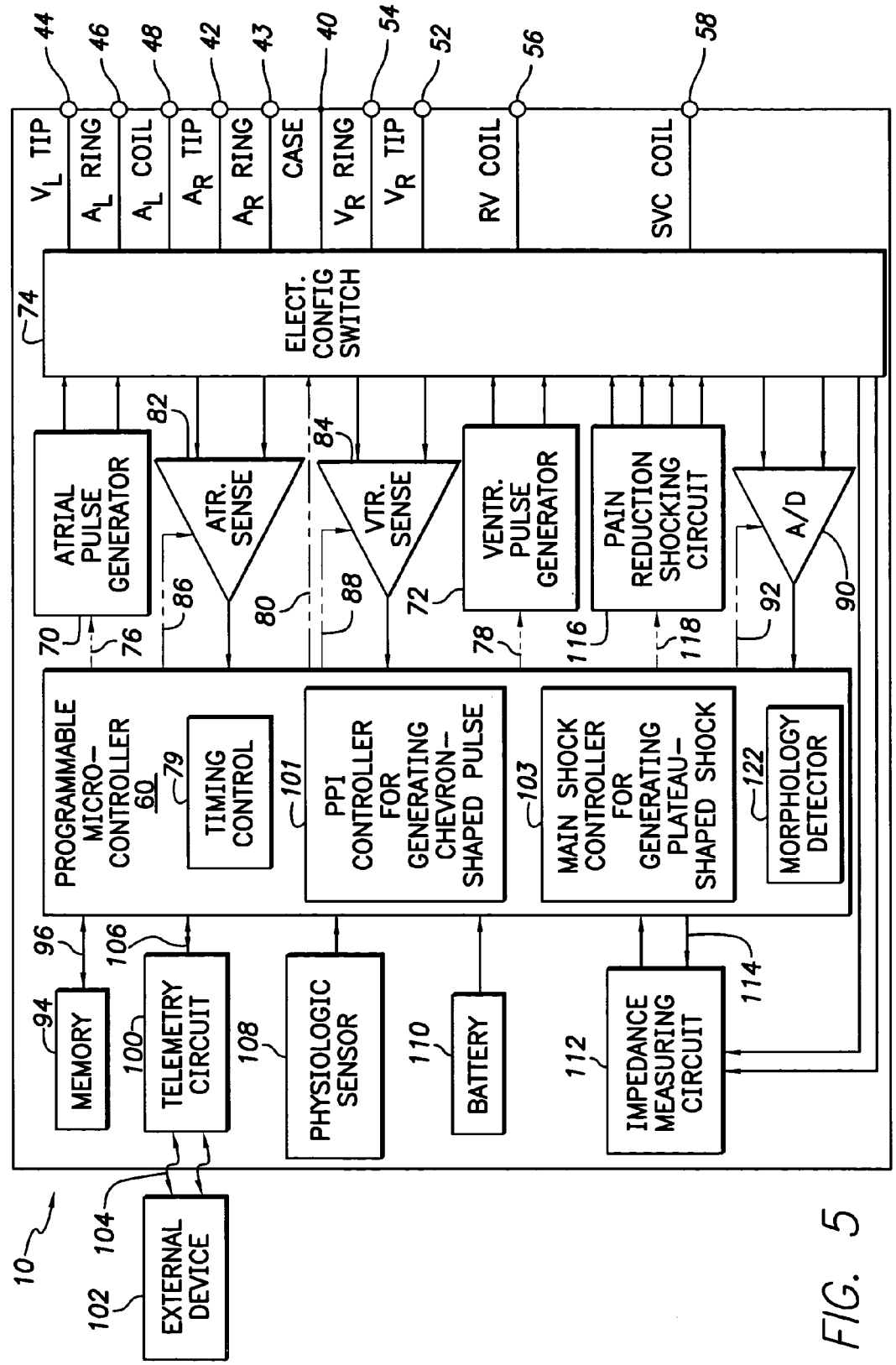
FIG. 5 is a functional block diagram of the implantable cardiac stimulation device of FIG. 4 illustrating basic elements of the stimulation device including components for controlling delivery of the improved plateau-shaped main shocks and the improved chevron-shaped PPI pulses.

As illustrated in FIG. 5, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 5, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 43, 44, 46, 48, 52, 54, 56 and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22. The connector also includes a right atrial ring terminal ($A_R$ RING) 43 adapted for connection to the atrial ring electrode 23. To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60, which controls the various modes of stimulation therapy. As is well known in the art, the microcontroller 60 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 5, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art. Switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art. Moreover, as the explained in greater detail below, the microcontroller transmits signals to controlling the switch to connect a different set of electrodes for different PPI pulses and main shocking pulses to enable the PPI pulses and shocking pulses to be delivered using different sets of electrodes.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers or shared amplifiers. The switch 74 determines the "sensing polarity" of the cardiac signal by selectively closing the appropriate switches, as is also known in the art. In this way, the clinician may program the sensing polarity independent of the stimulation polarity. Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Other pacing parameters include base rate, rest rate and circadian base rate.

Advantageously, the operating parameters of the implantable device 10 may be non-invasively programmed into the memory 94 through a telemetry circuit 100 in telemetric communication with the external device 102, such as a programmer, transtelephonic transceiver or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient.

The stimulation device additionally includes a battery or other power supply 110, which provides operating power to all of the circuits shown in FIG. 5. For the stimulation device 10, which employs shocking therapy, the battery 110 is capable of operating at low current drains for long periods of time, and then is capable of providing high-current pulses (for capacitor charging) when the patient requires a shock pulse. The battery 110 also has a predictable discharge characteristic so that elective replacement time can be detected. For example, the device 10 may employ lithium/silver vanadium oxide batteries. As further shown in FIG. 5, the device 10 is shown as having an impedance measuring circuit 112 that is enabled by the microcontroller 60 via a control signal 114.

To deliver cardioversion or defibrillation therapy, device 10 detects the occurrence of an arrhythmia of the type requiring such therapy, and automatically applies an appropriate electrical shock to the heart to terminate the arrhythmia. To this end, the microcontroller 60 further controls a pain reduction shocking circuit 116 by way of a control signal 118. The shocking circuit 116 generates shocking pulses of low (e.g., up to 0.5 joules), moderate (e.g., 0.5–10 joules) or high energy (e.g., 11 to 40 joules), as controlled by the microcontroller 60. Such shocking pulses are applied to the heart of the patient through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode). Cardioversion shocks for treatment of AF are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Pain reduction shocking circuit 116 also generates one or more chevron-shaped PPI pulses prior to a plateau-shaped cardioversion shock so as to reduce patient pain and hence is referred to herein as a pain reduction shocking circuit. The chevron-shaped PPI pulses are generated under the control of a PPI controller 101 within the microcontroller, i.e. controller 101 controls shocking circuit 116 to generate the PPI pulses and controls switch 74 to route the PPI pulses to the heart of the patient via selected combinations of electrodes. The plateau-shaped cardioversion shocks are generated under the control of a main shock controller 103 of the microcontroller, i.e. controller 103 controls shocking circuit 116 to generate the main shock and controls switch 74 to route the main shock to the heart of the patient via a potentially different combinations of electrodes. The operation of PPI pulse controller 101 and main shock controller 103 in combination with shocking circuit 116 and switch 74 is described below. Although shown as being part of the microcontroller, the PPI controller and the main shock controller may instead be implemented as components separate from the microcontroller.

Referring to the remaining figures, flow charts and other drawings provide an overview of the operation and novel features of stimulation device 10 as configured in accordance with exemplary embodiments of the invention. In the flow charts, the various algorithmic steps are summarized in individual "blocks". Such blocks describe specific actions or decisions made or carried out as the algorithm proceeds. Where a microcontroller (or equivalent) is employed, the flow charts provide the basis for a "control program" that may be used by such a microcontroller (or equivalent) to effectuate the desired control of the stimulation device. Those skilled in the art may readily write such a control program based on the flow charts and other descriptions presented herein.

Overview of Pain Reduction Technique

Figure 6:
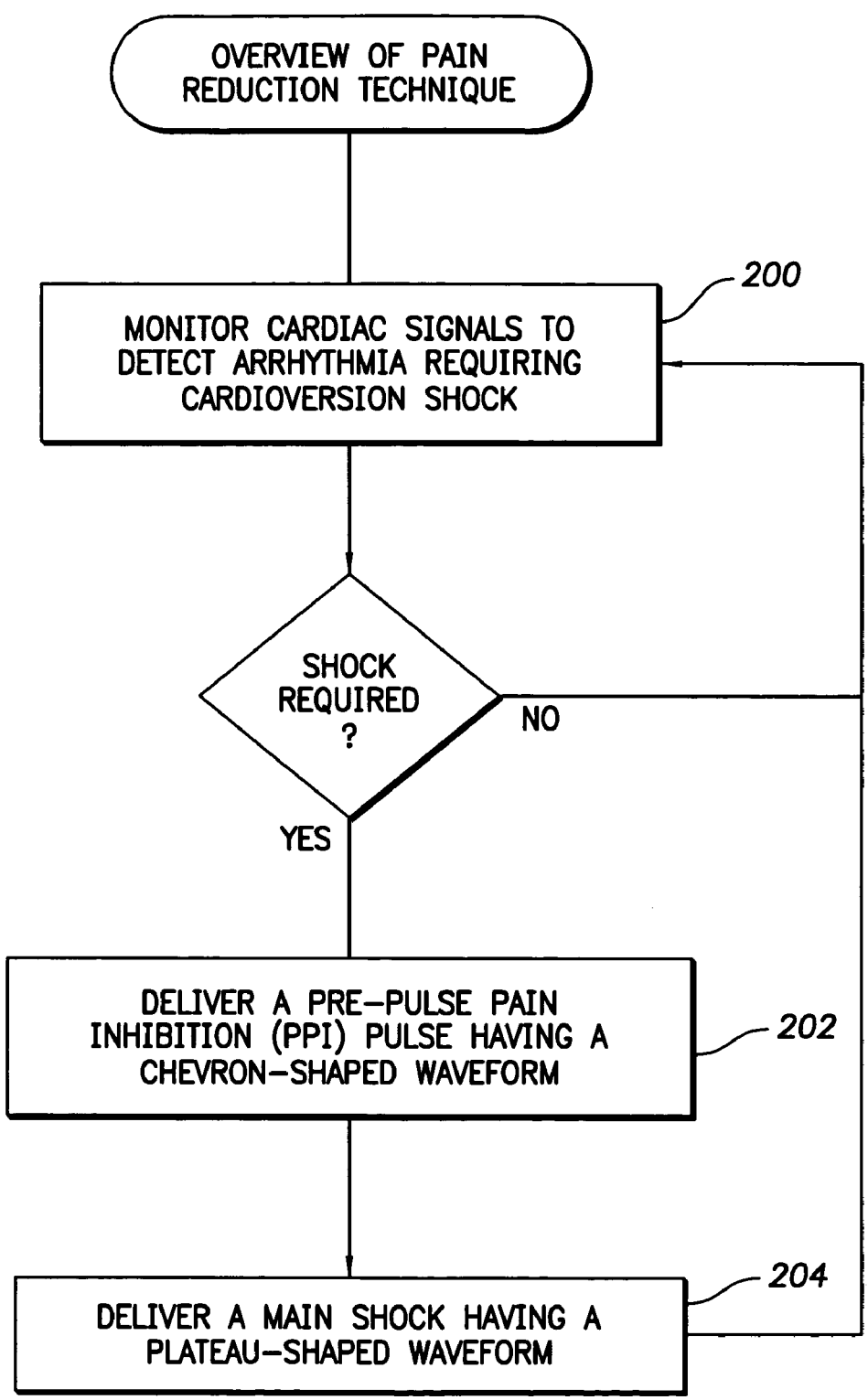
FIG. 6 is a flow chart providing an overview of a shock therapy technique, which provides a chevron-shaped PPI pulse followed by a plateau-shaped main cardioversion shock.

FIG. 6 illustrates operations performed by the implanted device of FIGS. 4–5 for use in reducing pain associated with cardioversion shocks applied to terminate AF. Similar steps may be performed to reduce pain associated with defibrillation shocks applied to terminate ventricular arrhythmias. Initially, at step 200, the implanted device inputs electrical cardiac signals from the leads illustrated in FIG. 4 and processes the signals to detect the onset of an arrhythmia requiring cardioversion, such as AF. In one implementation, to detect AF, the device tracks the atrial rate based on intrinsic P-waves and, if the atrial rate exceeds an AF detection threshold (AFDT), AF is presumed. In any case, if cardioversion is required, the implanted device then delivers one or more low-voltage PPI pulses each having a chevron-shaped waveform, at step 202. The low-voltage pulses are preferably delivered between electrodes within the heart and the device housing. Thereafter, a main shock having a plateau-shaped waveform is delivered, at step 204. The high-voltage main shock is preferably delivered between fairly closely adjacent electrodes implanted within the heart (such as between RV coil electrode 36 and SVC coil electrode 38 of FIG. 4) so as to concentrate shock energy in the cardiac tissue. The pulses generated by steps 202–204 are graphically illustrated within FIG. 7, which will be described in greater detail below.

Following delivery of the main cardioversion shock, processing returns to step 200 for further monitoring of the electrical cardiac signals to determine if the arrhythmia was properly terminated. If not, the PPI pulses are delivered yet again before a second cardioversion shock is delivered. Although not shown in FIG. 6, for AF, if several cardioversion shocks fail to defibrillate the atria, the implantable device may suspend further delivery of cardioversion shocks to permit the patient to seek medical attention. For VF, defibrillation shocks are repeatedly applied until VF is terminated, usually up to a maximum of six total shocks. In addition, although not shown, during step 200, overdrive pacing techniques may be employed to help prevent the onset of AF or VF. A particularly effective overdrive pacing technique for the atria, referred to as dynamic atrial overdrive (DAO) pacing, is described in U.S. Pat. No. 6,519,493 to Florio et al. A technique for providing multiple-tiered cardioversion and DAO therapy is described in U.S. patent application Ser. No. 10/374,835, of Kroll, entitled "System and Method for Providing Cardioversion Therapy and Overdrive Pacing Using an Implantable Cardiac Stimulation Device," filed Feb. 25, 2003. The techniques described therein, modified as needed, may be used in conjunction with the techniques of the present invention.

Figure 7:
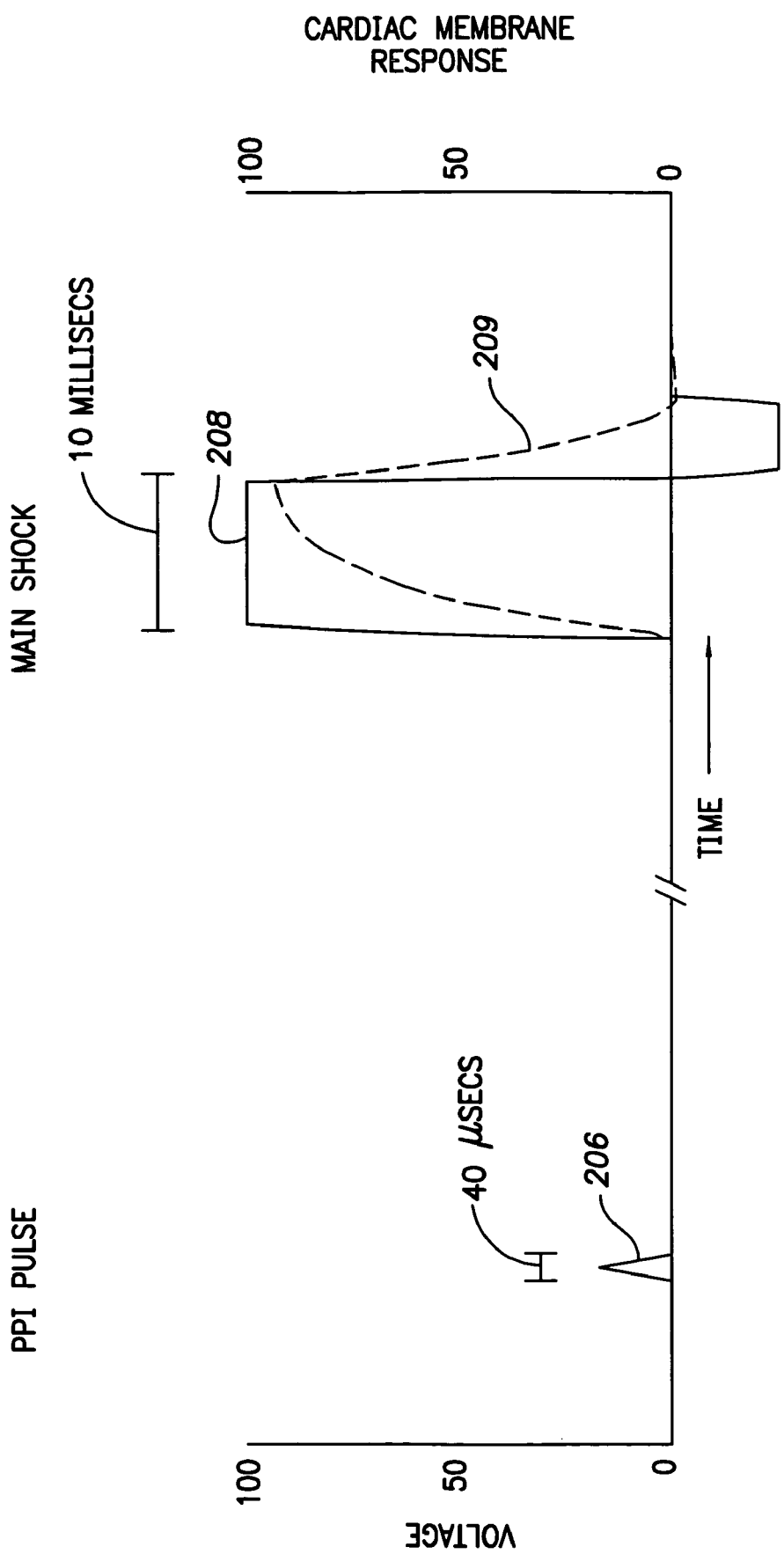
FIG. 7 is a graph illustrating exemplary chevron-shaped PPI pulse followed by an exemplary plateau-shaped main cardioversion shock generated using the technique of FIG. 6.

The chevron-shaped PPI pulse and the subsequent plateau-shaped main shock are shown in FIG. 7. Briefly, chevron-shaped PPI pulse 206 is an extremely short duration sliver pulse lasting only about 40 μs. Plateau-shaped main shock 208 is a biphasic shock having an overall duration of about 15 ms. Note that the horizontal time axis of FIG. 7 is not shown to scale due to great differences in pulse duration. In actuality, the 40 μs PPI pulse is 250 times shorter in duration than the plateau-shaped main shock. Instead, within FIG. 7, the horizontal time axis is shown as a "broken" axis to emphasize that the duration of the pulses is not to scale and to further emphasize that the time interval between the pulses is also not to scale. The PPI pulse has a peak voltage of only about 25 V whereas the main chevron plateau-shaped main shock has a peak voltage of about 100 V. The interval between the PPI pulse and main shock is programmable and may be set, for example, in the range of 30 to 500 ms. 80 ms is fairly typical. The duration may depend, for example, on the individual. The delivery of the main shock (and by implication the preceding PPI pulse) are also timed relative to ongoing electrical cardiac signals, in accordance with otherwise conventional techniques, so as to reduce the likelihood that either might be pro-arrhythmic and in particular to avoid triggering VF.

Figure 1:
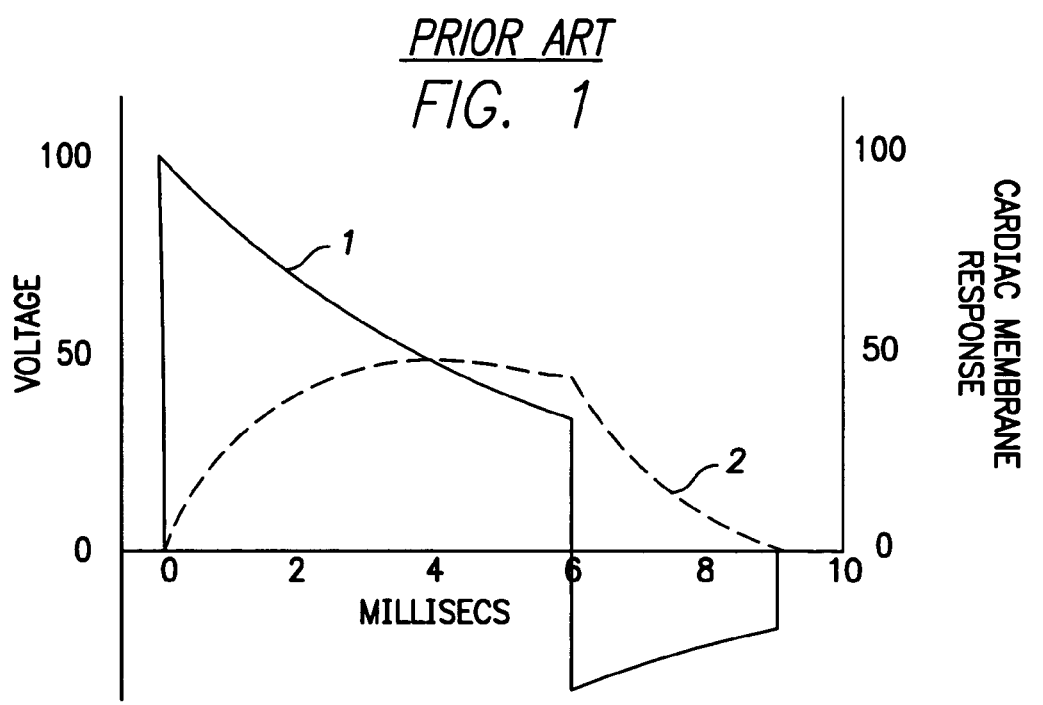
FIG. 1 is a graph illustrating a conventional non-smoothed main cardioversion shock waveform.
Figure 2:
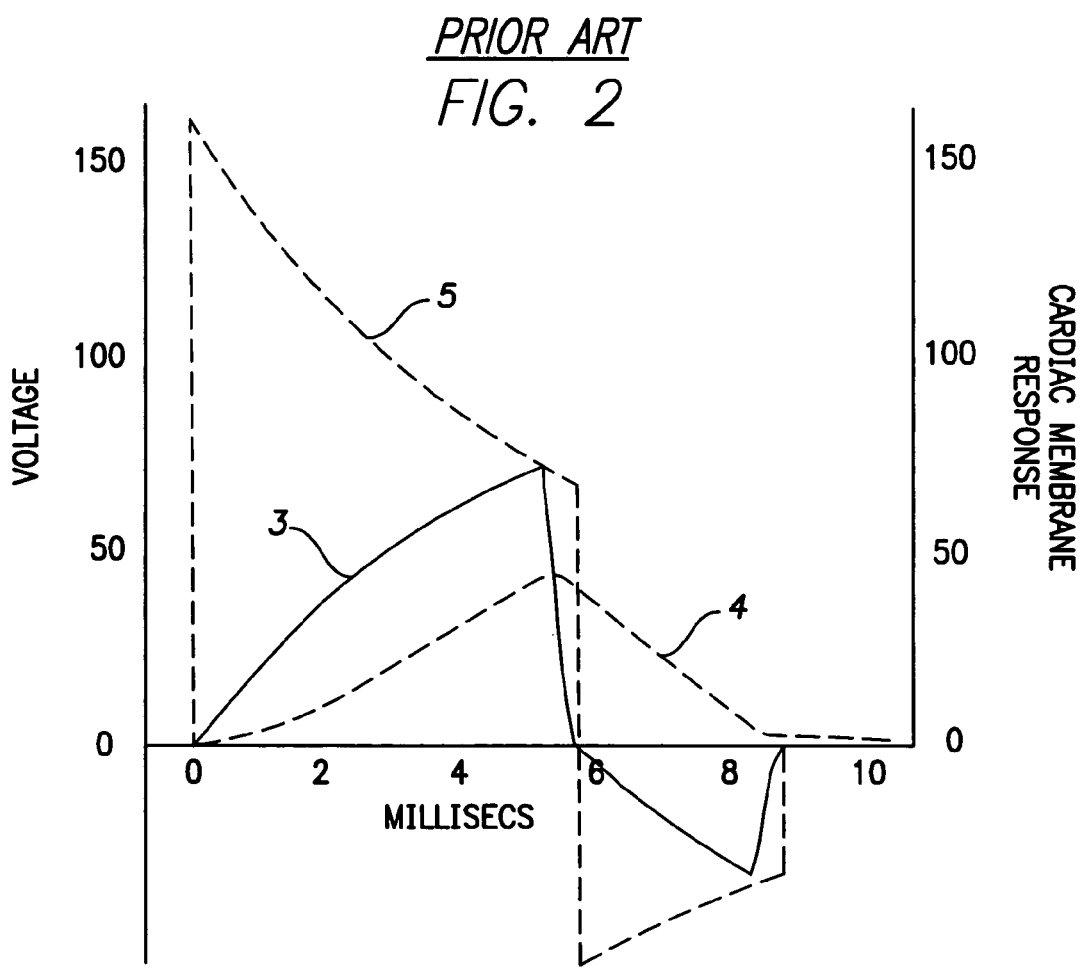
FIG. 2 is a graph illustrating a conventional smoothed main cardioversion shock waveform.

PPI pulse 206 serves to reduce the amount of pain perceived by the patient during the main cardioversion shock by distracting the brain. When the main shock sensation reaches the brain it is busy trying to form a perception of the PP pulse and is not able to fully "appreciate" the pain of the main shock. Volunteers have described the sensation as converting an otherwise extremely sharp pain into a much duller but longer pain. Since a relatively low-voltage is employed for the PPI pulse (only about 25 V), it can be advantageously delivered using widely spaced apart electrodes, such as between the RV tip electrode and the device housing, so as to provide a large antenna for activating a large number of nerve cells throughout the heart and thorax to achieve significant perception for the brain. The plateau-shaped of the main cardioversion shock also serves to reduce the amount of pain perceived by the patient. With the plateau-shaped waveform, pain reduction is achieved as compared to non-smoothed shocks or shocks smoothed in accordance with the conventional techniques discussed above with reference to FIG. 2, at least for equivalent peak voltages. In particular, a greater cardiac membrane response 209 is achieved at an equivalent peak voltage using the plateau-shaped waveform. Within FIG. 7, the cardiac membrane response is in the same arbitrary response units of FIGS. 1 and 2 for comparison purposes. As can be seen, for a peak voltage of 100 V, the cardiac response is over 90 units. In FIG. 1, a cardiac response of only about 50 units is achieved for a non-smoothed waveform at the same peak voltage of 100 V. In FIG. 2, a cardiac response of only about 45 units is achieved for a non-smoothed waveform at a peak voltage of 75 V. Alternatively, when using the smoothed waveform of FIG. 2, a cardiac response of about 60 units is achieved for a peak voltage of about 100 V. Hence, the plateau-shaped waveform can be used to achieve a substantially higher cardiac membrane response at the same peak voltage or can be used to achieve the same cardiac membrane response at a much lower peak voltage. Since peak voltage is a significant contributor to pain experience by the patient, a significant reduction in pain can be achieved by using the plateau-shaped waveform while still achieving the same level of shock effectiveness. In recent human studies, the plateau waveform has been shown to shift a perceived pain threshold by a factor of four, i.e. patients rate a plateau waveform delivered with 4 joules of energy as being no more painful than a conventional descending biphasic shock waveform delivered with 1 joule of energy.

Figure 3:
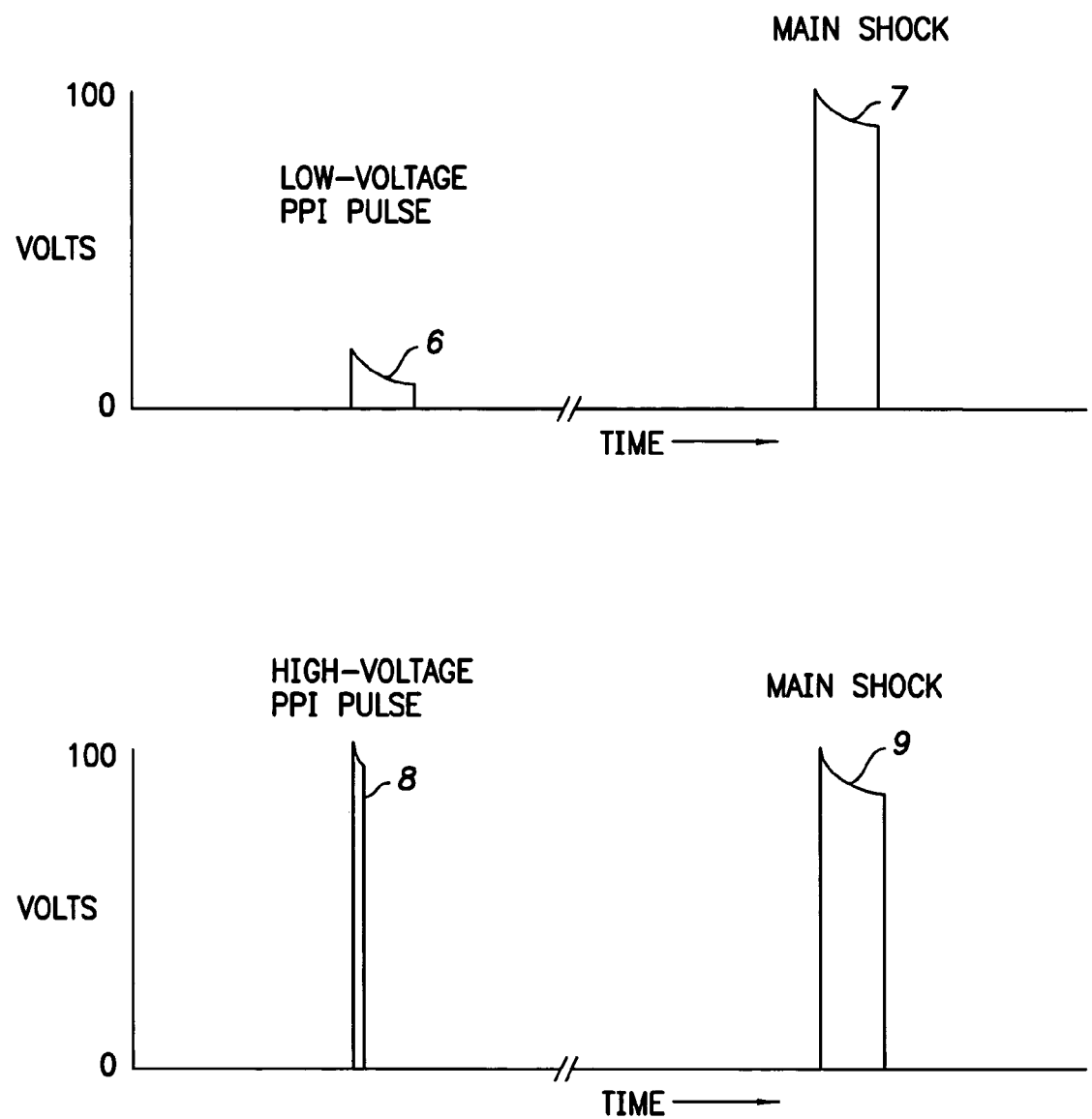
FIG. 3 is a graph illustrating conventional PPI pulses along with non-smoothed main cardioversion shocks.

Thus, both the PPI pulse and the plateau-shape of the main cardioversion shock serve to reduce patient pain. If desired, one technique or the other may be individually employed. In other words, a chevron-shaped PPI pulse may be employed prior to delivery of a conventional non-smoothed main cardioversion shock (such as the shock shown in FIG. 1) or prior to a conventionally smoothed main shock (such as the shock shown in FIG. 2.) Alternatively, conventional PPI pulses (such as those described above with reference to FIG. 3) may be delivered prior to the plateau-shaped main shock of FIG. 7. Preferably, however, both the chevron-shaped PPI pulse and the plateau-shaped main cardioversion shock are employed to achieve a significant enhancement in overall pain reduction for a given level of shock effectiveness. A particular advantage of using both the chevron-shaped PPI pulse and the plateau-shaped main shock is that a single circuit (shown in FIG. 8) may be employed to generate both waveforms using a single shock capacitor. In other words, despite the large voltage difference between the peak of the low-voltage PPI pulse and the peak of the high-voltage main cardioversion shock, a separate low-voltage shock capacitor is not required to generate the chevron-shaped PPI pulse.

Herein the term "chevron-shaped" is used to indicate that the PPI pulse generally has a V-shape or an inverted V-shape. The inverted V-shape is employed if the polarity of the shock is such that its peak voltage is negative rather than positive. In the example of FIG. 7, the voltage of the PPI pulse increases linearly from zero (or some other baseline voltage) to a peak voltage, then decreases linearly back to zero (or to the baseline voltage). In other examples, the increase and/or subsequent decrease may only be substantially linear, while still providing a generally V-shaped pulse. In addition, herein, the term "plateau-shaped" is used to indicate that the main pulse has a substantially flat peak. Depending upon the polarity of the shock, the flat peak may have a positive voltage or a negative voltage (relative to zero or relative to some other baseline voltage). In the case of a biphasic shock, the second phase of the shock will have the opposite polarity of the first phase. In the example of FIG. 7, the first phase of the main shock has a voltage that increases linearly during an initial short interval from zero up to a peak voltage, then remains at that peak voltage for a comparatively much longer interval of time, then decreases linearly during another short interval of time back to 0 V. The second phase of the shock has a similar shape, but inverted. In other examples, the increase and/or subsequent decrease may be only substantially linear and/or the peak may be only substantially flat, while still providing a generally plateau-shaped main shock. In the example of FIG. 7, the initial increase in voltage to the peal voltage occurs within about 0.5 ms, the voltage remains at its peak voltage for another 9 ms, then the voltage decreases within about 0.5 ms back to 0 V. These are merely exemplary values.

Pain Reduction Circuitry

Figure 8:
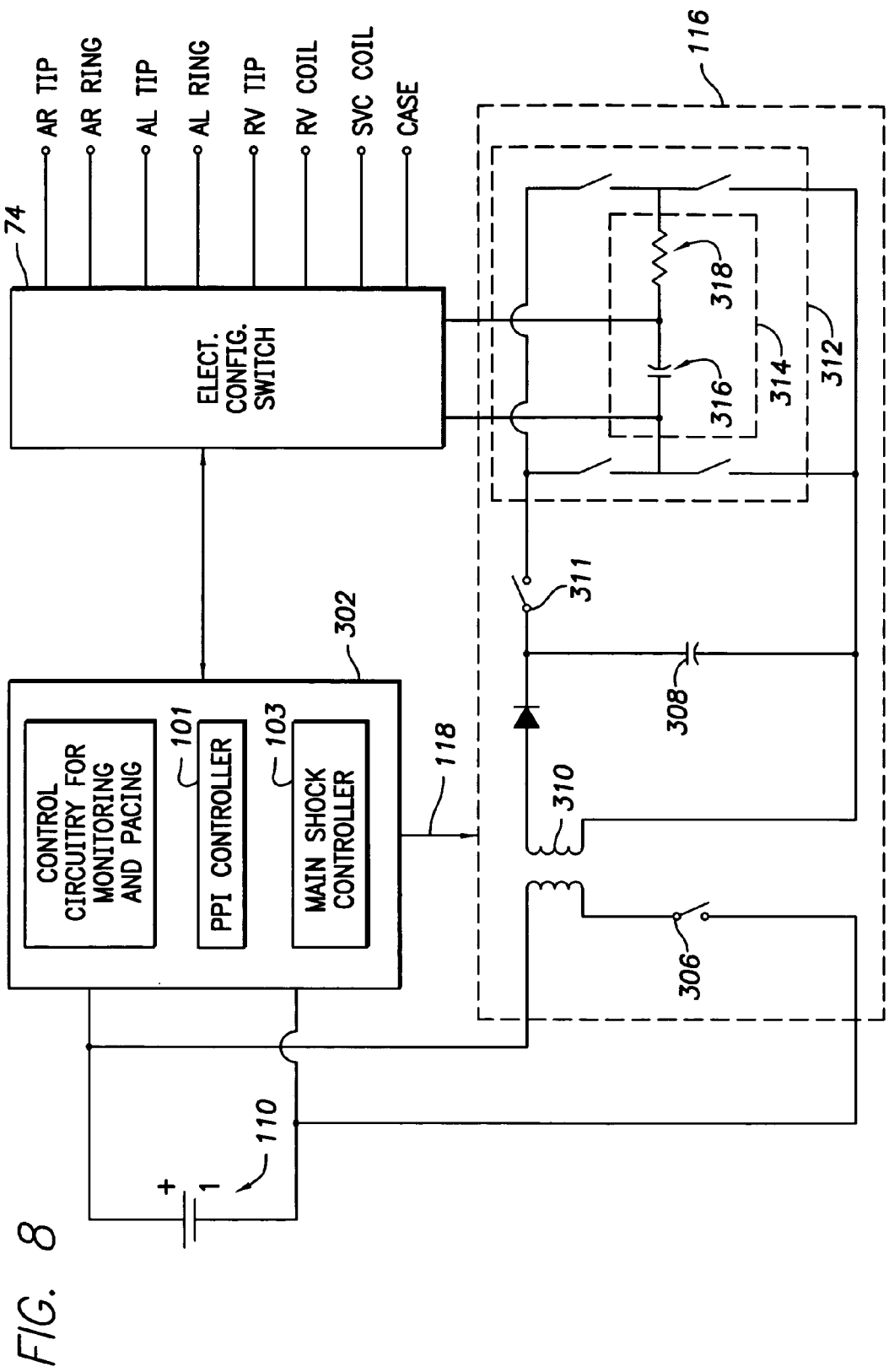
FIG. 8 is a diagram illustrating an exemplary circuit for generating both chevron-shaped PPI pulses and plateau-shaped main cardioversion shocks in accordance with the technique of FIG. 6.

Selected internal features of the implanted device of FIG. 5 are illustrated in FIG. 8. Battery 110 provides power for all monitoring and pacing functions, as well as for the generation of the chevron-shaped PPI pulses (under the control of PPI controller 101) and the generation of main cardioversion shocks (under the control of main shock controller 103.) For simplicity, in FIG. 5, a block 302 is used to collectively represent all pacing, monitoring and control circuit components (i.e. all device components shown in FIG. 5, with the exception of switch 74 and pain reduction shocking circuit 116.) Upon detection of an arrhythmia requiring cardioversion by control circuit 302, a control signal is sent along line 118 to pain reduction shocking circuit 116, which causes switch 306 to close to allow current from battery 110 to begin charging a high-voltage capacitor 308 via voltage transformer 310. Once the high-voltage capacitor has reached a predetermined maximum voltage (e.g. 200 V), a chopping switch 311 and an H-bridge switch 312 are controlled (by the signal on line 118) in accordance with a first switching sequence so as to route a small portion of the energy stored within capacitor 308 to electrode configuration switch 74 via a low-pass RC filter 314. More specifically, the chopping switch is held closed while capacitor 308 is discharged through the RC filter for about 20 µs, then the polarity is switched via the H-bridge for another 20 µs. The low-pass RC filter includes a capacitor 316 (which is much smaller than capacitor 308) and a resistor 316, configured as shown. The resistor and capacitor are sized and configured to provide, in this example, a low-pass RC filter time constant of about 100 µs. During the PPI pulse, the effect of the low-pass RC filter is to produce an output pulse having a chevron-shaped waveform. The PPI pulse is routed through switch 74, which operates under the control of the PPI pulse controller, to deliver the PPI pulse to the heart of the patient using, for example, the RV tip electrode with the device case as the return electrode. Note that the chopping switch simply remains closed during the generation of the PPI pulse. The chopping switch is more fully utilized during the generation of the subsequent main shock, as will be described below.

Figure 9:
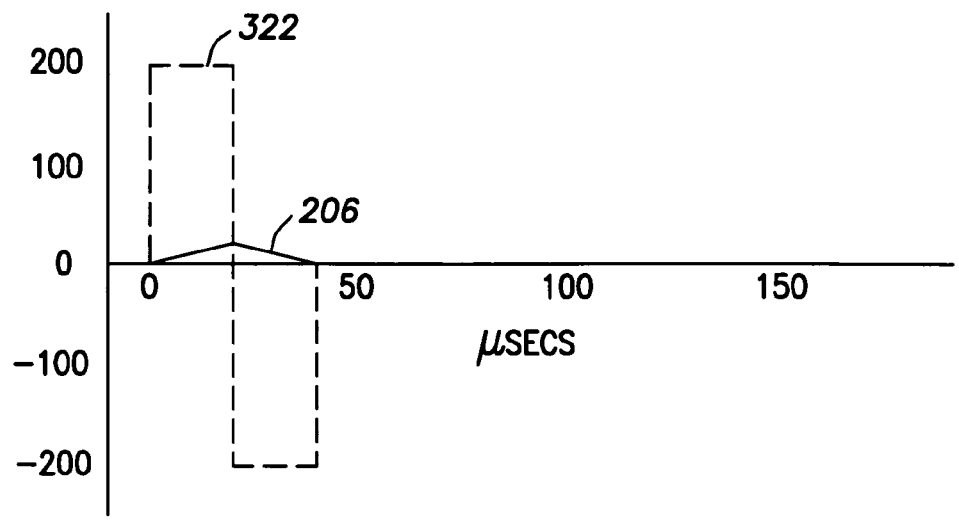
FIG. 9 is a graph particularly illustrating an exemplary chevron-shaped PPI pulse generated using the circuit of FIG. 8.

The resulting chevron-shaped PPI pulse (206) is shown within FIG. 9 along with a corresponding capacitor voltage profile 322, shown in phantom lines. The chevron-shape of the waveform is achieved as a result of the low-pass filter, i.e. the voltage of the PPI pulse waveform increases relatively slowly and substantially linearly due to the presence of the filter, while the voltage input to the filter remains near 200 V. Once the polarity is switched the voltage changes to −200 V, the voltage of the PPI pulse decreases linearly back to zero. As a result, the PPI pulse has an overall duration of 40 µs. Note that the capacitor voltage profile 322 does not show any decrease during either of the 20 µs phases. This is simply because the interval of time shown is so short that no noticeable decrease in voltage occurs. In actuality, a very slight decrease in voltage will occur in the capacitor voltage from its initial peak voltage of 200 V but that amount is not noticeable in the figure.

The 40 µs duration of the PPI pulse is determined primarily by the maximum switching speed of the H-bridge circuit. Current state-of-the-art switching circuits for use within implantable devices have a fastest possible switching speed of about 20 µs and hence a PPI pulse duration of 40 µs is the shortest duration that can easily be achieved at that switching speed. If desired, however, a somewhat slower switching speed, e.g. 25 µs can instead be employed to provide a somewhat longer duration PPI pulse, 50 µs, with a somewhat higher peak voltage. In the preferred embodiment described herein, the quickest possible switching speed is employed to generate the shortest possible PPI pulse so as to ensure a low peak voltage to allow use of the device housing as the return electrode. As noted, this allows for activation of a large number of nerve cells in the chest of the patient so as to achieve reliable perception and hence enhanced pain inhibition. If the duration of the PPI pulse is set to a somewhat longer duration, the peak voltage of the PPI pulse can rise to a point where it is equal to the capacitor voltage. If so, the PPI pulse is preferably delivered between a pair of electrodes implanted in the heart so as to reduce pain associated with the PPI pulse itself. Routine experimentation may be employed to identify a threshold voltage above which the PPI pulse should be delivered between electrodes in the heart. At still longer pulse durations, the PPI pulse will begin to adopt a plateau-shape, with a flat peak at the voltage of the capacitor. Hence, the circuit of the invention is not limited to generating chevron-shaped PPI pulses but is also capable of generating plateau-shaped PPI pulses, should those be desired. With still longer pulse durations, the pain associated with the PPI pulse itself may become too severe (even when delivered between a pair of electrodes in the heart) to be of value as a pain reduction pulse. Again, routine experimentation may be employed to identify a threshold duration beyond which the PPI pulse results in too much pain. At still longer durations, the voltage of the capacitor may decrease during generation of the PPI pulse by an amount requiring that the capacitor be recharged prior to delivery of the main shock.

Returning to FIG. 8, after the PPI pulse is delivered, the shopping switch is opened to prevent further discharge from the capacitor 308. A timer within control circuitry 302 is then activated to track the time interval before delivery of the subsequent main shock. When it is time for delivery of the main shock, the chopping switch and the H-bridge switch are then controlled by main shock controller 103 in accordance with a second switching sequence so as to deliver all or most of the remaining energy stored within capacitor 308 as a plateau-shaped main cardioversion shock. The plateau-shaped main shock is routed through switch 74, which operates under the control of the main shock controller, to deliver the main shock to the heart of the patient between, for example, the SVC coil and the RV coil.

Figure 10:
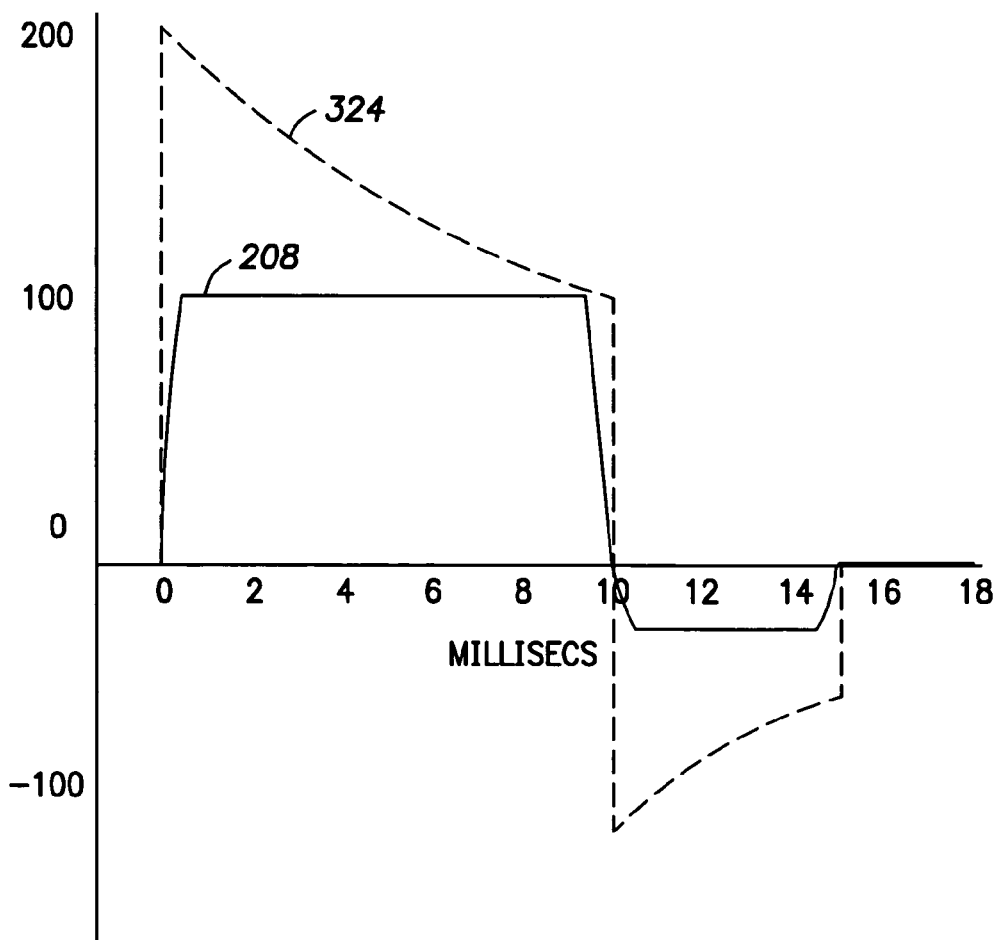
FIG. 10 is a graph particularly illustrating an exemplary plateau-shaped main cardioversion shock generated using the circuit of FIG. 8.

The resulting plateau-shaped PPI pulse (208) is shown within FIG. 10 along with a corresponding capacitor voltage profile 324, shown in phantom lines. As can be seen, the capacitor is again set to an initial voltage of 200 V and is discharged via the H-bridge circuit through the low pass filter with chopping switch 311 closed until the voltage of the output waveform reaches a peak voltage of about 100V. This takes about 0.5 ms, during which time the increase in voltage of the output waveform is substantially linear and its rate of increase is slowed by the filter. Next, the chopping switch is controlled so as to hold the voltage of the output waveform constant, while the capacitor voltage continues to decrease exponentially. More specifically, the chopping switch is toggled at a high switching rate by the main shock controller 103 so that the output voltage increases very slightly while the chopping switch is closed and decreases very slightly while the chopping switch is open to thereby hold the output voltage substantially constant while the capacitor discharges. In the example, of FIG. 10, the output voltage is held at 100V for about 9 ms, so as to produce a flat plateau voltage. During this interval of time, the capacitor voltage decreases exponentially down to about 100V and energy from the capacitor not delivered into the output shock is dissipated as heat. Then, the chopping switch is again held closed and the H-bridge is controlled so as to allow the voltage of the output waveform to drop to 0 V. This takes about 0.5 ms, during which time the decrease in voltage of the output waveform is substantially linear while the capacitor voltage continues to decrease exponentially. The H-bridge is then controlled to switch polarity and the process is repeated to produce the second phase of the main shock, which also has a plateau-shape. In the example of FIG. 10, the main shock has an overall duration of about 15 ms and its first phase is held at the peak plateau voltage of 100 V for 9 ms. These are merely exemplary values. Routine experimentation may be employed to identify voltage parameters and waveform shape parameters for maximizing shock effectiveness while minimizing the resulting pain in accordance with the principles of the invention. Also, in the example, for clarity the chopping switch is shown positioned between the main capacitor and the H-bridge. In general, though, it can be positioned at any suitable location within the circuit where it can operate to hold the voltage constant during the plateau phases, such as at a location within the H-bridge. The chopping switch and the H-bridge collectively comprise switching circuitry for selectively discharging the main storage capacitor through the low-pass RC filter for delivery to heart tissue of the patient. Other appropriate circuit configurations may instead be employed consistent with the principles of the invention described herein.

Thus, what we have described are various techniques for pain reduction particularly for use in connection with the delivery of cardioversion shocks, including defibrillation shocks. As can be appreciated, a wide variety of techniques can be implemented consistent with the principles the invention and no attempt is made herein to describe all possible techniques. Moreover, although described primarily with reference to a combined pacer/defibrillator, the techniques of the invention may be exploited for use with non-pacing ICDs. Various functional components of the exemplary systems may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention.

What is claimed is:

1. Shocking circuitry for use in an implantable cardiac stimulation device for implant with a patient, the shocking circuit being configured to generate a pre-pulse pain inhibition (PPI) pulse having a chevron-shaped waveform for application to the patient's heart and a plateau-shaped output shock waveform for application to the patient's heart.

2. The shocking circuitry of claim 1 comprising:
a main storage capacitor operative to hold a shock delivery charge;
a low-pass resistive-capacitive (RC) filter; and
switching circuitry operative to selectively discharge the main storage capacitor through the low-pass RC filter for delivery to heart tissue of the patient as either the plateau-shaped output waveform or the chevron-shaped output waveform.

3. The circuitry of claim 2 wherein the switching circuit includes an H-bridge circuit and a chopping switch.

4. The circuitry of claim 2 wherein the low-pass RC filter has a time constant of about 100 microseconds (µs).

5. The circuitry of claim 2 further including control circuitry operative to control the switching circuit to discharge the main storage capacitor through the low-pass RC filter to generate a main shock having a plateau-shaped waveform.

6. The circuitry of claim 5 wherein the control circuit is operative to control the switching circuit to discharge the main storage capacitor so as to
vary a shock voltage from a baseline voltage to a plateau voltage within a first short period of time;
maintain the shock voltage at substantially the plateau voltage for a significantly longer period of time; and
return the shock voltage to the baseline voltage within a second short period of time.

7. Original) The circuitry of claim 6 wherein the control circuit is operative to control the switching circuit to discharge the main storage capacitor so that the longer period of time is about nine times longer than the first and second short periods of time combined.

8. The circuitry of claim 6 wherein the control circuit is operative to control the switching circuit to discharge the main storage capacitor so that the first short period of time is about 0.5 milliseconds (ms), the longer period of time is about 9 ms, and the second short period of time is about than 0.5 ms.

9. The circuitry of claim 2 further including control circuitry operative to control the switching circuit to discharge the main storage capacitor through the low-pass RC filter to generate the pre-pulse pain inhibition (PPI) pulse having a chevron-shaped waveform.

10. The circuitry of claim 2 further including control circuitry operative to control the switching circuit to discharge the main storage capacitor through the low-pass RC filter to generate both the pre-pulse pain inhibition (PPI) pulse having a chevron-shaped waveform and a main shock having a plateau-shaped waveform.

11. The circuitry of claim 10 wherein the control circuit is operative to control the switching circuit to discharge the main storage capacitor so that the chevron-shaped waveform has a peak voltage substantially less than a peak voltage of the plateau-shaped shock.

12. The circuitry of claim 11 wherein the control circuit is operative to control the switching circuit to discharge the main storage capacitor so that the peak voltage of the chevron-shaped PPI pulse is about 25 volts (V) whereas the peak voltage of the plateau-shaped shock is about 250 V.

13. A system for use in an implantable cardiac stimulation device for implant within a patient, the system comprising:
a main shock controller configured to control generation of a plateau-shaped output shock waveform and a pre-pulse pain inhibition (PPI) pulse having a chevron-shaped output shock waveform; and
circuitry configured to output the selected waveform for delivery to heart tissue of the patient.

14. Shocking circuitry for use in an implantable cardiac stimulation device comprising:
storage means for holding a shock delivery charge;
filtering means for low-pass filtering a shock waveform; and
means for selectively discharging the storage means through the filtering means to selectively generate one or more of a plateau-shaped shock waveform and a chevron-shaped pre-pulse pain inhibition (PPI) pulse waveform for application to the patient's heart.

* * * * *